(12) United States Patent
Abid et al.

(10) Patent No.: US 11,948,298 B2
(45) Date of Patent: *Apr. 2, 2024

(54) SYSTEM TO COLLECT AND IDENTIFY MEDICAL CONDITIONS FROM IMAGES AND EXPERT KNOWLEDGE

(71) Applicant: Triage Technologies Inc., Toronto (CA)

(72) Inventors: Abdellatif Abid, Los Angeles, CA (US); Albert Jimenez Sanfiz, Toronto (CA); Adria Romero Lopez, Toronto (CA); Eric T. Jarmain, Toronto (CA); Mohamed Akrout, Toronto (CA); Anirudh Challa, Toronto (CA); Jeremy G. Kawahara, Nanaimo (CA); Stephen A. Solis-Reyes, London (CA)

(73) Assignee: Triage Technologies Inc., Toronto (CA)

( * ) Notice: Subject to any disclaimer, the term of this patent is extended or adjusted under 35 U.S.C. 154(b) by 201 days.

This patent is subject to a terminal disclaimer.

(21) Appl. No.: 17/468,068

(22) Filed: Sep. 7, 2021

(65) Prior Publication Data

US 2021/0407083 A1 Dec. 30, 2021

Related U.S. Application Data

(63) Continuation of application No. 17/122,329, filed on Dec. 15, 2020, which is a continuation of application (Continued)

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/441* (2013.01); *A61B 5/7267* (2013.01);
(Continued)

(58) Field of Classification Search
CPC ......... G06T 7/0012; G06T 2207/20076; G06T 2207/20081; G06T 2207/20084;
(Continued)

(56) References Cited

U.S. PATENT DOCUMENTS 8,693,788 B2    4/2014    Wojton
9,996,923 B2    6/2018    Thomas
(Continued)

FOREIGN PATENT DOCUMENTS

JP    2003126045    5/2003
JP    2004526141    8/2004
(Continued)

OTHER PUBLICATIONS

Akar, Esad, et al., "Cloud-Based Skin Lesion Diagnosis System using Convolutional Neural Networks", Intelligent Computing-Proceedings of the Computing Conference, Springer, Cham, 2019 (Year: 2019), 19 pages.
(Continued)

*Primary Examiner* — Md K Talukder
(74) *Attorney, Agent, or Firm* — Sheppard Mullin Richter & Hampton LLP

(57) ABSTRACT

Systems, methods, and storage media for automatically identifying medical conditions based on images and other data using machine learning methods and algorithms that encode expert knowledge of medical conditions. The systems, methods, and storage media may also leverage infrastructure that facilitates the collection, storage, labeling, dynamic organization, and expert review of existing and incoming data.

22 Claims, 11 Drawing Sheets

Related U.S. Application Data

No. 16/880,622, filed on May 21, 2020, now Pat. No. 10,878,567.

(60) Provisional application No. 62/902,354, filed on Sep. 18, 2019.

(51) Int. Cl.
*G06V 10/764* (2022.01)
*G06V 10/82* (2022.01)

(52) U.S. Cl.
CPC .......... *A61B 5/7275* (2013.01); *G06V 10/764* (2022.01); *G06V 10/82* (2022.01); *G06T 2207/20076* (2013.01); *G06T 2207/20081* (2013.01); *G06T 2207/20084* (2013.01); *G06T 2207/30088* (2013.01); *G06T 2207/30168* (2013.01)

(58) Field of Classification Search
CPC . G06T 2207/30088; G06T 2207/30168; G06T 2207/20088; A61B 5/441; A61B 5/7267; A61B 5/7275; A61B 5/444; A61B 5/1032; A61B 5/107; A61B 5/0013; A61B 5/0033; A61B 5/0077; G06V 10/764; G06V 10/82; G06F 18/24137
See application file for complete search history.

(56) References Cited

U.S. PATENT DOCUMENTS

| | | | |
|---|---|---|---|
| 10,055,551 | B2 | 8/2018 | Agaian |
| 10,192,099 | B2 | 1/2019 | Agaian |
| 2009/0082637 | A1 | 3/2009 | Galperin |
| 2018/0108442 | A1* | 4/2018 | Börve ................... G16H 50/70 |
| 2019/0171914 | A1 | 6/2019 | Zlotnick |
| 2019/0220967 | A1 | 7/2019 | Bhatt |
| 2020/0211692 | A1* | 7/2020 | Kalafut ................. G06N 20/00 |
| 2020/0294234 | A1* | 9/2020 | Rance ..................... G06F 18/22 |
| 2021/0012493 | A1* | 1/2021 | Jiang .................. G06Q 30/0641 |
| 2021/0118550 | A1* | 4/2021 | Rahman ................... G06N 3/08 |

FOREIGN PATENT DOCUMENTS

| | | |
|---|---|---|
| JP | 2005192944 | 7/2005 |
| JP | 2016510223 | 4/2016 |
| JP | 2016174728 | 10/2016 |
| JP | 2019079503 | 5/2019 |
| JP | 2019079503 A | 5/2019 |
| WO | 2015035229 | 3/2015 |
| WO | 2016159379 | 10/2016 |

OTHER PUBLICATIONS

Akrout, Mohamed, et al., "Improving Skin Condition Classification with a Question Answering Model", in Medical Imaging Meets NeurIPS Workshop, 32nd Conference on Neural Information Processing Systems (NIPS 2018), 2018, pp. 1-4.

Akrout, Mohamed, et al., "Improving Skin Condition Classification with a Visual Symptom Checker Trained Using Reinforcement Learning", in MICCAI, vol. 2, Springer International Publishing, 2019, doi:10.1007/978-3-030-32251-9, pp. 549-557.

Ballerini, Lucia, et al., "A Color and Texture Based Hierarchical K-NN Approach to the Classification of Non-Melanoma Skin Lesions", in Color Medical Image Analysis, Lecture Notes in Computational Vision and Biomechanics, vol. 6, Springer Netherlands, 2013, doi:10.1007/978-94-007-5389-1_4, pp. 63-86.

Celebi, M. Emre, et al., "A Methodological Approach to the Classification of Dermoscopy Images", Computerized Medical Imaging and Graphics, vol. 31, No. 6, 2007, doi:10.1016/j.compmedimag.2007.01.003, pp. 362-373.

Demyanov, Sergey, et al., "Tree-Loss Function for Training Neural Networks on Weakly-Labelled Datasets", in IEEE International Symposium on Biomedical Imaging, 2017, doi:10.1109/ISBI.2017.7950521, pp. 287-291.

Demyanov, Sergey, et al., "Classification of Dermoscopy Patterns Using Deep Convolutional Neural Networks", IEEE 13th International Symposium on Biomedical Imaging (ISBI), Apr. 13-16, 2016, doi:10.1109/ISBI.2016.7493284, pp. 364-368.

Esteva, Andre, et al., "Dermatologist-Level Classification of Skin Cancer with Deep Neural Networks", Nature, Volumn 542, No. 7639, 2017, doi:https://doi.org/10.1038/nature21056, pp. 115-126.

Google Health Announcement, "Using AI to Help Find Ansewrs to Common Skin Conditions", <URL: https://blog.google/technology/health/ai-dermatology-preview-io-2021/>, May 18, 2021, 5 pages.

Google Health Dermatology, <URL: https://health.google/health-research/imaging-and-diagnostics/#dermatology>, printed Jul. 1, 2021, 11 pages.

Google Health Health, <URL: https://health.google/>, printed Jul. 1, 2021, 11 pages.

Jimenez, Albert, et al., "Class-Weighted Convolutional Features for Visual Instance Search", in Proceedings of the 28th British Machine Vision Conference, 2017, arXiv:1707.02581v1, pp. 1-13.

Kawahara, Jeremy, et al., "Seven-Point Checklist and Skin Lesion Classification Using Multitask Multimodal Neural Nets", IEEE Journal of Biomedical and Health Informatics, Volumn 23, No. 2, Mar. 2019, doi:10.1109/JBHI.2018.2824327, pp. 538-546.

Patnaik, Sourav Kumar, et al., "Automated Skin Disease Identification Using Deep Learning Algorithm", Biomedical & Pharmacology Journal, vol. 11, No. 3, Sep. 2018 (Sep. 2018), DOI: https://dx.doi.org/10.13005/bpj/1507, available from http://biomedpharmajournal.org/?p=22169, pp. 1429-1436.

Romero Lopez, Adria, et al., "Skin Lesion Classification from Dermoscopic Images Using Deep Learning Techniques", in IASTED International Conference Biomedical Engineering. IEEE, 2017, doi:10.2316/P.2017.852-053, pp. 49-59.

Ummadisetti, Ravichandu, et al., "Hierarchical Classification of Skin Cancer Images", Dissertation Indian School of Business, 2018 (Year: 2018), 37 pages.

* cited by examiner

Metrics — 602

| | True Predictions | False Predictions | Accuracy |
|---|---|---|---|
| Top - 1 | 4603 | 1705 | 75.0% |
| Top - 2 | 5449 | 861 | 86.4% |
| Top - 3 | 5755 | 554 | 91.2% |
| Top - 4 | 5878 | 431 | 93.2% |
| Top - 5 | 5955 | 354 | 94.4% |

Confusion Matrix (at Top-1) — 604

|  |  | Actual |  |  |  |  |
|---|---|---|---|---|---|---|
| | Class | Good | Blowout | Dark | Distant | Blurry |
| Predicted | Good | 192 (85.7%) | 8 (36.4%) | 2 (3.1%) | 7 (5.1%) | 10 (15.2%) |
| | Blowout | 5 (2.2%) | 11 (50.0%) | 0 (0.0%) | 0 (0.0%) | 2 (3.0%) |
| | Dark | 8 (3.6%) | 0 (0.0%) | 59 (92.2%) | 2 (1.4%) | 1 (1.5%) |
| | Distant | 13 (5.8%) | 2 (9.1%) | 2 (3.1%) | 127 (92.0%) | 2 (3.0%) |
| | Blurry | 6 (2.7%) | 1 (4.5%) | 1 (1.6%) | 2 (1.4%) | 51 (77.3%) |

FIG. 6

SYSTEM TO COLLECT AND IDENTIFY MEDICAL CONDITIONS FROM IMAGES AND EXPERT KNOWLEDGE

CROSS-REFERENCE TO RELATED APPLICATIONS

This application is a continuation of U.S. patent application Ser. No. 17/122,329, filed Dec. 15, 2020, which is a continuation of U.S. patent application Ser. No. 16/880,622, filed May 21, 2020 (which issued as U.S. Pat. No. 10,878,567 on Dec. 29, 2020), which is a non-provisional patent application of U.S. Patent Application Ser. No. 62/902,354, filed Sep. 18, 2019, the contents of which are incorporated by reference in their entirety for all purposes.

FIELD OF THE DISCLOSURE

The present disclosure relates to a system that automatically identifies medical conditions based on user supplied images and other data using machine learning methods and algorithms that encode expert knowledge of medical conditions, and leverages infrastructure that facilitates the collection, storage, labeling, dynamic organization, and expert review of existing and incoming data.

BACKGROUND

Medical diseases are common health concerns worldwide and affect people of all ages, genders, and races. The prevalence of various medical conditions include skin disease, cardiovascular disease, diabetes, and obesity. For example, one in five Americans is predicted to develop skin cancer by the age of 70, and malignant skin lesions are considered to be critical public health and clinical concerns.

Developing computer systems that can reliably recognize objects within images has been a longstanding challenge and has been the subject of considerable research efforts. Prior attempts to provide an application to visually identify medical conditions from images have faced various drawbacks. Better systems and methods are needed.

BRIEF SUMMARY

According to various embodiments of the disclosed technology, a system, a computer-implemented method, and/or computer readable medium may be configured to determine medical conditions from an image uploaded to a medical condition classification application that are processed within the medical condition classification application or uploaded to a server.

For example, a server may be configured for determining medical conditions from images uploaded to a medical condition classification application that are processed within the medical condition classification application or uploaded to a server, the system comprising one or more hardware processors configured by machine-readable instructions to: store one or more datasets of medical condition images, wherein the medical condition images are tagged with labels and probabilities corresponding to the medical conditions made by human experts; train a visual classifier model with the one or more datasets of the medical condition images; receive, via a user interface of the medical condition classification application, an uploaded image of a portion of the affected medical; pass the uploaded image through a visual classifier model to determine a context of the uploaded image; generate an output of a visual classifier model representing predicted probabilities that the uploaded image falls into one or more medical condition classes; determine a set of predictions for the medical condition classes using the refined probabilities; display the set of predictions (or at least a portion of the set) that the uploaded image falls into on a computer display via the user interface; display information about the set of predictions; and display exemplar medical disease images of the set of predictions or medical disease that are similar to the uploaded image.

In some embodiments, the system will invoke a question module that selects and presents queries based on the predicted probabilities and confidence levels for the uploaded image; receive responses to the queries via the user interface; and iteratively present queries and refine the predicted probabilities based on the received responses.

In some embodiments, the one or more datasets of validated images of medical conditions is generated by generating within the system a queue of images managed by the system to be presented to the human experts, the one or more datasets of validated images of medical conditions is generated by presenting a second image to a predetermined number of the human experts via the user interface, the one or more datasets of validated images of medical conditions is generated by receiving and storing labels and corresponding probabilities for the image from each of the human experts, the one or more datasets of validated images of medical conditions is generated by combining the reviews made by multiple human experts, and the one or more hardware processors are further configured by machine-readable instructions to remove the image from the queue and store the labels and corresponding probabilities with the image. In some embodiments, the uploaded image and the second image may be the same image. In some embodiments, the uploaded image and the second image may be different images.

In some embodiments, presenting the image includes presenting the image via one or more user interfaces, and presenting the image includes providing a set of user interface display elements prompting the human expert to input whether the image meets the required parameters, appears to be healthy skin or other body part, displays diseased skin or other body part, and the corresponding probabilities of specified medical diseases, is a poor quality image, or a measure of the probability that the human expert does not know how to correctly label the image.

In some embodiments, the step of determining whether the image meets a stored set of required parameters will consider an image and additional user supplied information in a multi-gate module, where the multi-gate module may incorporate a visual classifier to determine that the image meets the required parameters, and to generate an output that directs the image to modality specific modules or indicates the image does not meet the required parameters.

In some embodiments, the one or more datasets of validated images of medical conditions comprising of labeled images mapped to an ontology which maintains relationships between dermatological conditions, the ontology comprising nodes representing medical conditions, which have parent-child relationships, the method further comprising linking related medical conditions with broader labels to specific, situational disease labels.

In some embodiments, the one or more hardware processors are further configured by machine-readable instructions to organize the datasets into a data structure comprising a hierarchical structure.

In some embodiments, the one or more hardware processors are further configured by machine-readable instructions to: present a user interface through which an administrative user can create and manage image review tasks.

In some embodiments, expert reviews of the uploaded image are combined and provided to the user that uploaded the uploaded image in order for the user to receive the set of predictions that exist with the uploaded image based on the opinion of multiple experts.

In some embodiments, a method may be configured to perform the operations described by the system outlined herein. In some embodiments, a non-transient computer-readable storage medium having instructions embodied thereon, the instructions being executable by one or more processors to perform the operations described by the system outlined herein.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

BRIEF DESCRIPTION OF THE DRAWINGS

The present disclosure, in accordance with one or more various embodiments, is described in detail with reference to the following figures. The figures are provided for purposes of illustration only and merely depict typical or example embodiments.

FIG. 6 illustrates example metrics and visualizations used to measure the predictive performance of the system, in accordance with an embodiment of the disclosure;

DETAILED DESCRIPTION

Figure 1:
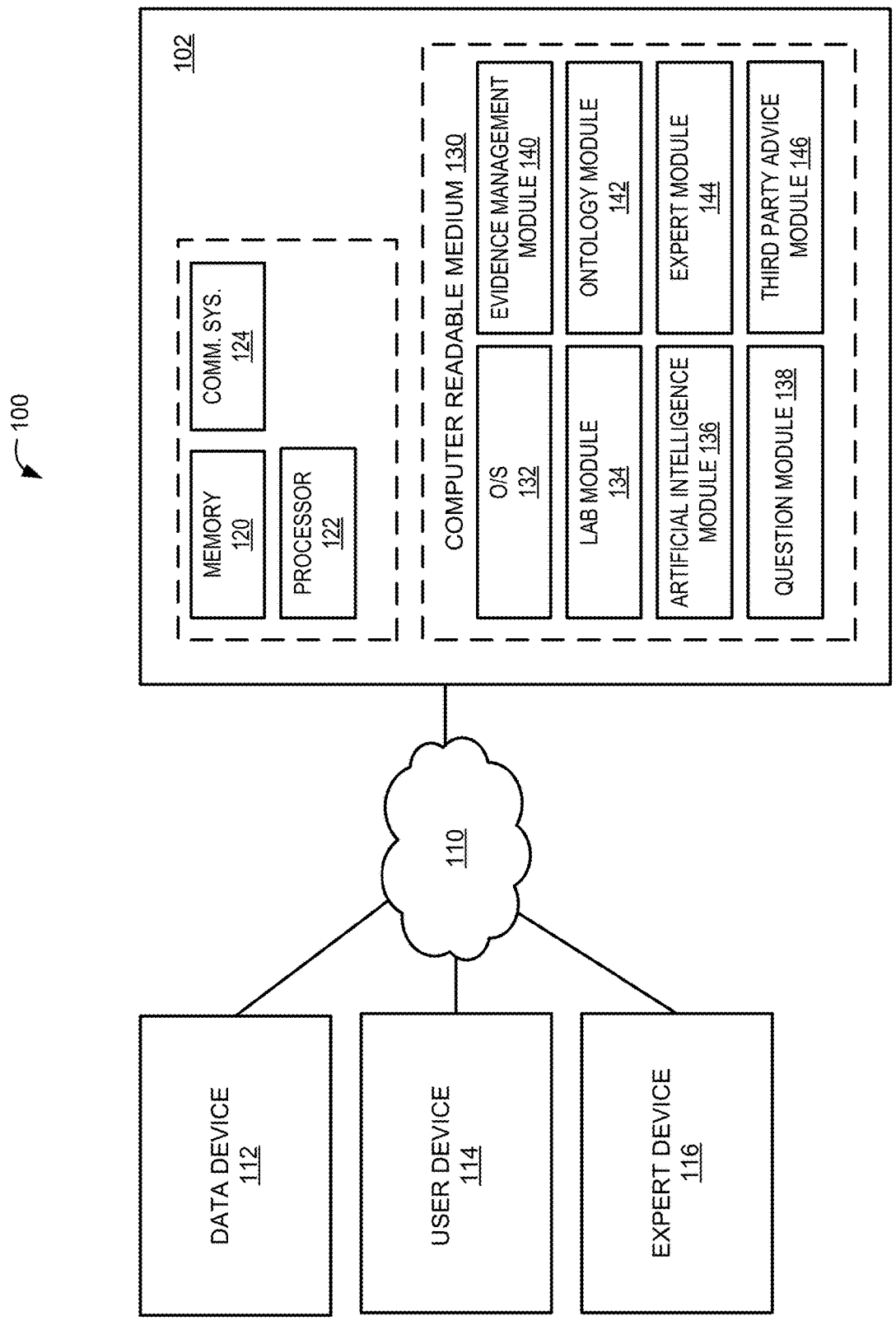
FIG. 1 illustrates a medical condition system with a plurality of devices that may interact within a single integrated system locally or across a distributed network, in accordance with an embodiment of the disclosure.

One aspect of the present disclosure relates to a system configured to identify medical conditions from images (e.g., through a mobile camera or other imaging device) and other uploaded data (e.g., age of patient and/or other patient data) and may be processed locally within the system, sent to a server (e.g., a web server hosting a website), or a combination of local and remote processing. The concepts of the disclosure can be applied to classifying images involving various medical conditions and non-medical topics as well. For simplicity, the description may focus primarily on identifying skin or generic medical conditions. Also for simplicity, the term "image," "images," or "one or more images" may be used interchangeably, but may include other types of data, including videos. It is to be understood that the principles of the disclosure can be applied to various forms of media and multi-modal data (e.g., video, stereo, depth, metadata, and other media and/or data).

The method may include storing one or more datasets of images of medical conditions in a database. The images may be tagged with labels corresponding to medical conditions and/or other informative tags. The method may include: training a visual classification model to identify medical conditions using one or more datasets of medical condition images and meta-data; organized using one or more ontologies that may relate to one or more specific conditions; receiving via an interface of the application various user specific information, such as age, sex, the location of the body where the medical condition occurs and/or other user specific information, and uploaded images of the skin or other body part and associated meta-data; passing the images through a multi-gate module in order to determine the general context of the images and direct the images to the appropriate models or actions; computing predicted probabilities for the uploaded images into one or more medical condition classes; invoking a question module that selects and presents via the application, queries based on the predicted probabilities of the uploaded image; receiving responses to the queries via the user interface; refining the predicted probabilities based on the received responses and user specific information; displaying at least some of the refined predictions that the uploaded image falls into one or more medical condition classes on a display via the user interface; and displaying images that are visually and clinically similar to the uploaded image(s) on a digital display via the user interface.

One aspect of the disclosure relates to a system that employs artificial intelligence (AI), big data, and analytic technologies to incorporate deep learning, computer vision, and algorithms that encode expert knowledge of medical diseases. For example, the system may predict medical conditions by combining a visual classifier, trained on a dataset of medical images, with a question module that encodes the users' responses to questions based on expert knowledge of medical conditions.

According to one aspect of the disclosure, new, incoming images to the system may be reviewed by a panel of experts (e.g., medical collaborators). In order to be more robust to the uncertainty of a single diagnosis and to better mimic the dermatologists' process of providing a differential diagnosis, each medical collaborator may assign (e.g., via a user interface) multiple candidate medical condition labels to an image. The assigned labels may be ranked or assigned a confidence value that indicates the predicted probability of each candidate condition. These candidate medical condition labels and predicted probabilities may be stored and/or added to the dataset of medical images, where the predicted probability for the medical condition labels may be combined across the medical collaborators that reviewed the specific image. This allows the system to be trained on the labels and predicted probabilities of each label that a group of medical experts make on a broad dataset, increasing the robustness of the system when making predictions on new cases, including generating refined probabilities. The system may leverage online machine learning and other forms of machine learning.

The system generates predictions for images uploaded by users as described herein. However, new images can come from a variety of other sources and may be obtained as a function of the various integrated modules described herein. For example, the disclosure may include a telehealth or teledermatology module, where users send images and other information to medical professionals and on which a medical opinion is provided, and this information may be added to the dataset. Images may also come from clinicians who use the technology in their practice in a manner that may include uploading images through a system integrated into their workflow and may be used on patients during clinical practice, used on an existing database of past patients, or both. Images may also come from other sources as detailed herein.

The system may utilize a survey delivered via a user interface to experts, such as doctors, to collect medical condition information, establish the structure of a clinical ontology, and receive examples of various medical conditions. The survey data may be processed to generate a knowledge base of medical conditions. The survey may allow doctors to answer condition-specific questions (e.g. demographic prevalence), upload example images, provide metadata or context for images, provide a diagnosis, differential diagnoses, and predicted probabilities associated with each diagnosis, and provide associated symptoms in addition to appearance (e.g. itchiness, pain, etc.). This medical condition data may be utilized to train and test the system and develop the algorithms that encode expert knowledge of medical conditions.

One aspect of the disclosure includes a technology-based approach to capture information that is not readily available within images alone and that may be relevant to diagnosing a patient. For example, doctors may ask patients questions to narrow down the plausible conditions in order to diagnose their patients more efficiently. The system includes an automated approach that diagnoses patients based on images, patient-specific information (such as age, sex, affected body location and/or other patient-specific information), and a sequence of questions and their corresponding answers, and uses machine learning to continually improve the technology.

The system may include one or more hardware processors configured by machine-readable instructions to perform the functions described herein. The system may be configured to store one or more datasets in the manner described. The images may be tagged with labels corresponding to medical conditions. The system may be configured to train a visual classifier model with one or more datasets of images of medical conditions. The system may be configured to receive via a user interface of the application uploaded images that capture the affected skin or other body part. The system may be configured to pass the uploaded images through a multi-gate module that determines the general context of the images and directs the images to the appropriate models or actions. If the multi-gated module determines the image(s) shows a medical condition, the image(s) are passed to a subsequent medical-classification model. This medical-classification model computes refined probabilities from the predicted probabilities and other input that the images fall into various medical condition classes. The predictions may be refined by incorporating any additional user supplied information and a question module. Once the system determines the relevant information has been asked of the user (or the maximum number of questions to ask is reached), these predicted conditions are displayed to the user.

The system may be configured to generate an output of the visual classifier model(s) including refined probabilities that represent the likelihood that the uploaded image(s) exhibits one or more medical condition classes. The system may be configured to invoke a question module that selects, and presents via the application, queries determined based on the visual predicted probabilities and other additional information. The system may be configured to receive responses to the queries via the user interface. The system may be configured to refine the predictions based on the received responses. The system may be configured to display the refined predictions that the uploaded image falls into one or more medical condition classes on a digital display via the user interface. The system may be configured to display images that are visually and clinically similar to the uploaded image(s) on a digital display via the user interface.

The system may serve a variety of applications such as a standalone system to help identify potential diseases based on images and other supplied information; and/or an integrated system into a telehealth platform to help triage patients prior to being seen by a clinician.

Medical Condition System and Devices

The system may include a distributed network that leverages a set of modules (e.g. computer software modules programmed in a hardware processor) that work together to provide numerous advantages, including visual identification of images of medical conditions. In some instances, some modules may be combined to work locally (e.g., on an image capture device) without data being sent over a network. In some cases, images may be processed locally and then the data is sent to a server for storage in the system.

FIG. 1 illustrates a medical condition system with a plurality of devices that may interact within a single integrated system locally or across a distributed network, in accordance with an embodiment of the disclosure. In illustration 100, medical condition system 102 communicates via network 110 with a plurality of devices and data sources, including the data device 112, the user device 114, and the expert device 116. For example, as one or more of the plurality of devices and data sources upload images, the system may be configured to predict the medical condition associated with the images in real-time.

Medical condition system 102 may comprise memory 120 coupled with processor 122 and communication subsystem 124. Processor 122 can be implemented as one or more integrated circuits and can be used to control the operation of medical condition system 102. Processor 122 can execute a variety of programs in response to program code or computer readable code stored in computer readable medium 130 and can maintain multiple concurrently executing programs or processes. Communication subsystem 124 may include one or more communication connections that can be used by medical condition system 102 to communicate directly with other devices, including the data device 112, the user device 114, and the expert device 116, and/or to connect with these devices via network 110 (external or internal) or through other means.

Memory 120 can be implemented using any combination of nonvolatile memories (e.g., flash memory), volatile memories (e.g., DRAM, SRAM), computer readable medium 130, or any other non-transitory storage medium or combination thereof. Computer readable medium 130 may store operating system 132 to be executed by processor 122. In some embodiments, operating system 132 may implement one or more software or hardware modules that can be invoked to implement one or more features described herein. For example, computer readable medium 130 may store lab module 134, artificial intelligence module 136, question module 138, evidence management module 140, ontology module 142, expert module 144, and/or third-party advice module 146.

Lab module 134 may be configured to act as a central system that manages and tracks many aspects of the system's operations including: data storage and management, model training, evaluation of results, maintaining ontologies, and coordinating review tasks where images are labeled by external specialists. Lab module 134 may provide systematic coordination, synchronization, tracking, and analysis across various sets of functionality (e.g., models, datasets, ontologies and review tasks) in a sophisticated, comprehensive, and accountable way.

Lab module 134 may be configured to leverage ontologies. An ontology is a hierarchical tree structure, which maintains relationships between dermatological or other medical conditions. The tree structure includes nodes representing medical conditions, which have parent-child relationships, linking related conditions with broader labels to specific, situational disease labels. Images in datasets may be associated with one or more nodes in the tree structure. The tree structure may be used to determine training classes: individual or groups of clinically related conditions used to train the models.

Lab module 134 may be configured to store and manage models and create model snapshots. A model snapshot may correspond with a frozen, point-in-time version of a machine learning model. For example, a model snapshot may be a convolutional neural network (CNN) architecture together with its weights. Once a model is uploaded, evaluations can be run from the lab module 134 on test data. Evaluation results and statistics can be displayed via a portion of the lab module 134 (e.g., an evaluations tab). A unique identifier may be assigned to each of the evaluations, with the set of images (Dataset snapshot) and specific machine learning model (Model snapshot). A summary of the evaluation metrics may be provided and tracked as well. This provides a consistent, centralized, permanent location for the management, recording, and display of metrics from the evaluation of experiments. Lab module 134 may be configured to record and display machine learning processes by coordination, synchronization, tracking, and analysis across the sets of functionality (e.g., models, datasets, ontologies, and review tasks).

Lab module 134 may be configured to dynamically evaluate model snapshots. Model snapshots may include data, output, and parameters for past and current versions of the models used by the system. Lab module 134 may use evaluation results to automatically compare different model versions and determine the best models to deploy and use. Lab module 134 may be configured to automatically deploy the best models to artificial intelligence module 136.

Lab module 134 is configured to manage images provided from various data sources. For example, lab module 134 may receive an image and adjust it (e.g., cropping the image, etc.) or the image may be adjusted at a user device prior to receiving the image at lab module 134. Every image may be associated with one or more datasets, which are collections of related images. Lab module 134 is configured to allow users to upload new images individually (e.g., in JPG, GIF, or PNG formats), or upload compressed archive files with multiple images (e.g., in ZIP format). Lab module 134 may provide an interface to view a historical list of uploads (e.g., uploaded filenames, uploader name, date of upload, and the number of images uploaded). Lab module 134 may be configured to detect duplicate or near-duplicate images by comparing the pixel values and other image meta-data. Upon detecting duplicate or near-duplicate images, the lab may deduplicate uploaded images by merging or overwriting existing metadata in its data store. Images detected as duplicate or near-duplicate may be tagged for review.

Lab module 134 may be configured to allow users to manually add or remove tags to specific images in datasets (e.g., via a user interface). Tags are a form of metadata attached to images, and may take the form "key:value", where a "key" specifies the type or category of tag, while "value" specifies the value within that type or category. For example, some tags could be "animal:cat" and "animal:dog". Images may have one or more associated tags. Lab module 134 is configured to search, browse, and access images, for example, by means of queries on tags.

Lab module 134 is configured to automatically add specified tags on images in specific scenarios. For example, lab module 134 may be configured to add the tag "lab:not-square" on images which are not square. In some examples, lab module 134 may be configured to automatically query an external application programming interface (API) and apply tags on images based on the result. In some examples, lab module 134 may be configured to use one or more of the models to classify images, and apply tags on images based on the result. In some examples, lab module 134 may be configured to apply tags based on reviews made in expert module 144.

Lab module 134 may be configured to allow users to create, manage, and use dataset snapshots. Dataset snapshots may correspond with frozen point-in-time snapshots of a particular subset of the images stored in the database of the lab module 134. When a set of images are used to evaluate or train a model, lab module 134 is configured to facilitate and track this process by identifying and extracting a specific subset of the image inventory by means of user queries on the presence or absence of tags on the images.

Lab module 134 may be configured to allow users to download or run evaluations on prior snapshots. Snapshots are preserved and do not change, even if more images are later added or re-labeled in the data inventory. This allows for control and consistency in snapshots to maintain their integrity through future evaluations to ensure reproducibility of results.

Lab module 134 may be configured to optionally separate the images into different partitions (e.g., based on limiting files to a predetermined threshold value, based on dynamically-determined partitions, or based on fractional partitions, etc.). In some examples, the user may choose unique names for each data partition and may specify the criteria to partition the images. In some examples, the system provides the option of randomly selecting images by a maximum number of images for each data partition (for example, if there are 1000 images of shoes, by selecting "100", a subset of 100 random shoe images will be selected from the 1000 total shoe images) and by percent of total images (selecting 50% would yield 500 images of shoes using the previous example). If images are cropped, the cropped images may be downloaded in their cropped state or original uncropped images with an associated file that indicates the cropping coordinates. In some examples, the user may omit data partitions, for example, if the total number of images within the partition is less than a desired number of images.

Lab module 134 may be configured to isolate images given specific criteria via a queue. Once the criteria are set, if an image fits the characteristics in the queue, those images may be accessible for viewing and modification. As opposed to a snapshot, queues may reflect the latest state of the data in the lab, including any new uploads or image modifications.

Lab module 134 may be configured to provide an interface to allow for modification of a plurality of image tags at once (i.e., a bulk modify operation). For example, the interface may provide functionality to add, edit, and remove tags from a select group of images (e.g., via tag query, snapshot, upload, queue or from a list of image IDs). Lab module 134 may be configured to provide an interface to permanently hide images. Hidden images can remain in any previous existing snapshots, but would be restricted from the creation of new snapshots.

Artificial intelligence module 136 may be configured to receive and provide an image to a visual identification component (e.g., a visual classifier). Artificial intelligence module 136 may implement one or more learning algorithms to utilize additional information associated with images. Convolutional neural networks (CNNs), or other neural network models, may be implemented for making predictions from images.

Artificial intelligence module 136 may rely on stochastic gradient descent or other types of optimization algorithms to optimize the neural networks. For example, evolutionary methods (genetic algorithms) and/or "credit assignment learning algorithms," which includes algorithms that use any type of weight update rule including backpropagation and evolutionary methods, may be used. The disclosure may leverage Neural Architecture Search (NAS).

Artificial intelligence module 136 may be configured to consider different Convolutional Neural Networks (CNNs). For example, an implementation may use a wide variety of CNN architectures with different configurations, e.g., varying the number of layers, the size of the convolutional filters, the size of the pooling layers, the use of regularization techniques, etc. An ensemble of architectures and techniques may be used to improve performance.

Various data normalization techniques may be used to pre-process the data before passing the data into the networks. For example, mean subtraction, which involves subtracting the mean pixel values of the images within a dataset from each image, may be used.

Different types of model weight initializations may be used. For example, weights may be randomly initialized, weights may be initialized using weights that were trained over different visual object recognition tasks (e.g., ImageNet database), or a combination of approaches may be used.

Different methods may be used when processing the data and choosing the network's hyperparameter values. For example, to determine effective model configurations, models may be combined with varying weighted loss functions, network regularization techniques, and data augmentation techniques.

The visual classification system may involve using an ensemble of Convolutional Neural Networks (e.g., Inception version 3, Inception ResNet version 2, and DenseNet and/or other CNNs); applying data normalization when pre-processing the images; initializing the model weights from models pre-trained on other datasets (e.g., ImageNet); applying different regularization techniques during training, such as dropout and batch normalization; and addressing the dataset class imbalance by adding class weights to the loss function and/or using over-sampling techniques.

Artificial intelligence module 136 may be configured to implement one or more machine learning models, using one or more classifiers. A classifier may include an algorithm trained to label input samples. One example of a classifier is a medical condition classifier, where medical conditions may be classified using a visual classifier trained with labelled images. Upon receiving and classifying the image, the system may list N (e.g., N=5) possible output predictions to the user. In some examples, each image may undergo multiple random perturbations or distortions. The perturbed image may be passed through the classifier multiple times, and the probabilities from each perturbed image may be aggregated to form the final predictions. In some examples, upon receiving more than one image or multiple frames in a video corresponding to the affected skin or other body part, the system may aggregate the probabilities from each image or frame to form a final list of predictions.

Artificial intelligence module 136 may be configured to train the model. For example, the training process may provide the visual classifier and other modules (e.g., question module 138, etc.) with samples (e.g., images) and corresponding probabilities for each label derived from the combined reviews of experts. Given the training samples, the model is trained to predict the label probabilities made by the combined expert reviews. If a visual classifier is trained with images of medical conditions, it may learn features from the training data that allow it to differentiate each medical condition group. If a new image is presented, the visual classifier can process the image and identify candidate medical condition labels with predicted probabilities for each label.

Artificial intelligence module 136 may be configured to use various evaluation metrics to evaluate its prediction performance. Metrics may include, for example, accuracy, cross-entropy, sensitivity, specificity, precision and/or other metrics. Any one or more of these factors may be used to evaluate the model's prediction performance.

Artificial intelligence module 136 may be configured to leverage many models, either independently or in combination with other models. Each model may be sensitive to specific images features by applying different training techniques and model architectures. Artificial intelligence module 136 may be configured to use metrics that measure the performance of the trained models to weigh the contribution of each model to the predicted medical conditions. Some factors to consider include the performance of detecting a specific class, and the complexity of the model (e.g., the number of layers, the number and type of connections between layers).

Artificial intelligence module 136 may be configured to dynamically train the models. For example, as new reviewed data becomes available, artificial intelligence module 136 may incorporate the new data and retrain the model(s). The performance of the updated model may be reviewed using an internal set of labelled images. If the performance is improved, the updated model may be released into a production environment, improving the model available to users.

Artificial intelligence module 136 may interact with other modules of the system (e.g., question module 138) and provide initial candidate diagnoses and differentials that may be refined by the additional modules.

Question module 138 may be configured to generate and transmit relevant questions, which may be based on the preliminary candidate conditions and predicted probabilities computed from the visual classification of the image(s), to further narrow down the initial predicted medical condition classes. This question asking process may rule out or confirm potential medical conditions. By first providing an image to the visual classifier, the possible medical conditions and the questions selected can be more targeted (e.g., to focus on the probable medical conditions as determined by the visual classifier).

Question module 138 may be configured to terminate a question and answer process, in some examples, when a set maximum number of questions have been asked, or when the system determines the questions relevant to the candidate predicted medical disease classes have been addressed by the user.

The system may be configured to put more importance on the answers of different questions depending on the relevance of the question to the specific medical disease. Question module 138 may refine the initial predicted probabilities associated with each predicted medical condition to improve the quality of the diagnoses shown to the user and generate a refined probability.

Question module 138 may be configured to use the information provided to provide questions and adjust the probabilities of the candidate conditions (including excluding candidate medical conditions that conflict with information provided by the user). For example, if a candidate medical condition is "melanoma", a question that may be asked is "Has your medical condition recently changed its color, size, or shape?" This encodes known medical knowledge that an important indicator of melanoma is a skin lesion that is changing in color, size, or shape. The questions and corresponding responses may be associated with each image.

Question module 138 may be configured to generate questions and to incorporate user supplied information (e.g., age, sex, and body location the lesion occurs on). For example, question module 138 may use the visual classifier's prediction probabilities (e.g., from artificial intelligence module 136) from the uploaded image as predicted probabilities to determine the questions to ask patients (e.g., use a technological approach to imitate the clinician-patient dialogue needed to arrive at a diagnosis). Question module 138 may be configured to select relevant questions from a predefined list of questions, where the answers may maximize the information gain with respect to determining probable medical predictions. Question module 138 may refine the classification probabilities of the visual classifier system based on the answers after each question.

Question module 138 may be configured to incorporate a CNN with a Reinforcement Learning (RL) agent. This may decrease the average number of questions needed to narrow down the differential diagnoses. A RL agent may learn how to ask the patient about the presence of symptoms in order to maximize the probability of correctly identifying the underlying condition. The RL agent may use the visual information provided by the CNN in addition to the answers to the asked questions to guide question module 138. The RL-based approach may increase the performance compared to the CNN approach, as the CNN relies on the visual information to predict the conditions.

Evidence management module 140 may be configured to monitor the evidence received by the system and may conclude the final predicted diagnoses based on multiple sources of evidence (e.g. predictions from artificial intelligence module 136 and question module 138, medical records, expert opinions, etc.). Evidence management module 140 may access the predictions from multiple sources of evidence made at different granularities within the ontology and project and combine them over a shared standardized ontology. Evidence management module 140 may also combine multiple opinions.

Evidence management module 140 may be configured to monitor system performance and may ask experts for more information if the results are inconclusive at some step of the inference process by transmitting data via the network 110 to expert device 116.

Ontology module 142 may be configured to represent the relationships among dermatological conditions, where the ontology includes nodes that may represent the medical conditions, and edges that may represent the relationships among conditions. The ontology may encode, for example, dermatological condition labels at different levels of granularity, from broad general labels to specific, situational disease labels. The dermatology ontology structure may be derived and/or extended based on established medical ontologies (e.g., SNOMED CT, etc.). Other ontologies may be used to classify other medical subjects.

Ontology module 142 may be configured to identify conditions that have a similar pathophysiology or clinical relationships. As the dataset may include images labeled with varying degrees of label granularity or specificity of the medical condition, the ontology may be used to aggregate the images labeled at different granularities into common groupings used by the visual classifiers (e.g., class labels used to train a visual classifier). For example, Nodular Basal Cell Carcinoma (NBCC) is a subtype of Basal Cell Carcinoma (BCC). This relationship may be encoded within the ontology through representing NBCC as a child of BCC. Based on this relationship, a BCC training class label may be formed with images labeled as BCC as well as NBCC. The grouping of conditions may also be dependent on the number of images associated with each ontology node. These condition groupings are stored and used to determine the mapping of the visual classifier output with the grouping of medical condition labels.

As an image may have multiple labels with probability values assigned to each label, an image may be associated with one or more nodes within the ontology. The probability value assigned to each label may indicate a fractional contribution of the image to the number of images associated with an ontology node.

Ontology module 142 may be visualized through the ontologies function in lab module 134, where information such as the ontology codes, corresponding human-readable label, and number of images associated with each node may be shown and edited.

Expert module 144 may be configured to facilitate the review of images by providing images and associated patient data (e.g., age of patient if known) to one or more expert devices 116 for human expert feedback. Human expert feedback for an image may include gathering: candidate medical conditions and corresponding probabilities for the image, whether the medical condition in the image appears to be of healthy skin or other body part, of poor quality, or that the human expert cannot determine the condition from the image.

Expert module 144 may be configured to provide an image to up to N (e.g., N=5) human experts (e.g., dermatologists, etc.) via expert device 116, where each expert may perform the review task. After N experts have reviewed the image, the review for that image may be stopped. An image is considered validated and usable for training and evaluation once it receives reviews from M (e.g., M=3) number of experts. A creator of an image review task may select the minimum number M and maximum number N of experts to review an image.

Expert module 144 may be configured to receive and store the reviews in order to extend the dataset of medical condition images. The reviews (e.g., the labels and corresponding probabilities) made by multiple experts may be combined to form a probabilistic labelling of each image. Images may be organized and labelled with codes and associated probabilities that map within a clinical ontology (e.g., ontology module 142) or other custom list.

Expert module 144 (in association with lab module 134, etc.) may be configured to provide the combined image reviews made by expert users back to the user that originally uploaded the image. The combined image reviews may be provided to a user interface of the user device 114.

Third party advice module 146 is configured to integrate third party applications to receive additional data. For example, a third party application may include a telemedicine, teledermatology, or other third party application that receives images and diagnoses from experts. The information from the third party application may be received via communication subsystem 124 and provided as training or testing data to artificial intelligence module 136.

Additionally, the features and capabilities of the system may be leveraged in other ways. For example, third party applications may operate independently and as standalone applications (e.g., telemedicine, etc.). Third party advice module 146 may be configured to integrate a third party module with the system to achieve a synergistic result compared with a stand-alone third party application. For example, the integration of the third party application with the other system components (e.g., visual classifier and question module) can provide improvements over prior systems. As an example, when an end user invokes the third party advice module 146 and uploads an image, artificial intelligence module 136 may make a prediction as to the medical conditions associated with the image and question module 138 may present questions for the end user based on the initial predictions. All of this information may be presented to the provider to increase the efficiency of the system.

As detailed below, the integration of these functions into a single platform provides many synergies. One aspect of the disclosure relates to the integration of the various functionalities and their interaction to provide improved results and a continually improving dataset.

Figure 2:
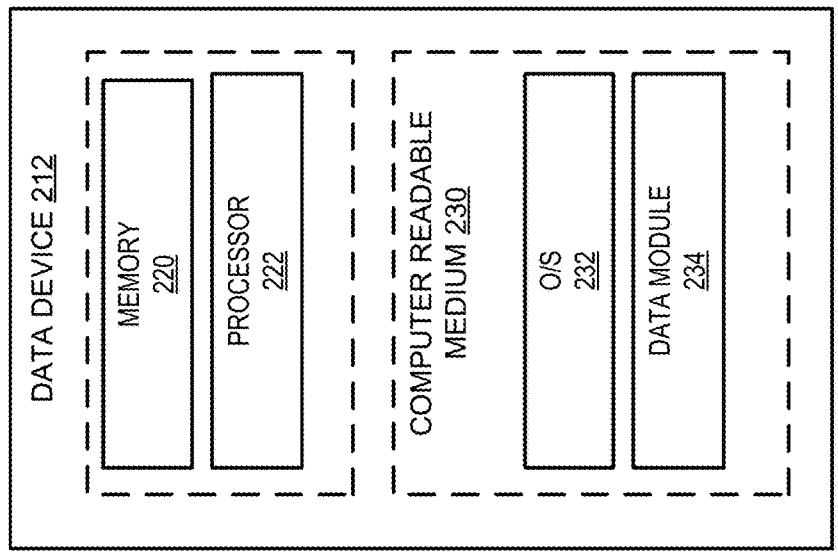
FIG. 2 illustrates a data device, in accordance with an embodiment of the disclosure.
Figure 3:
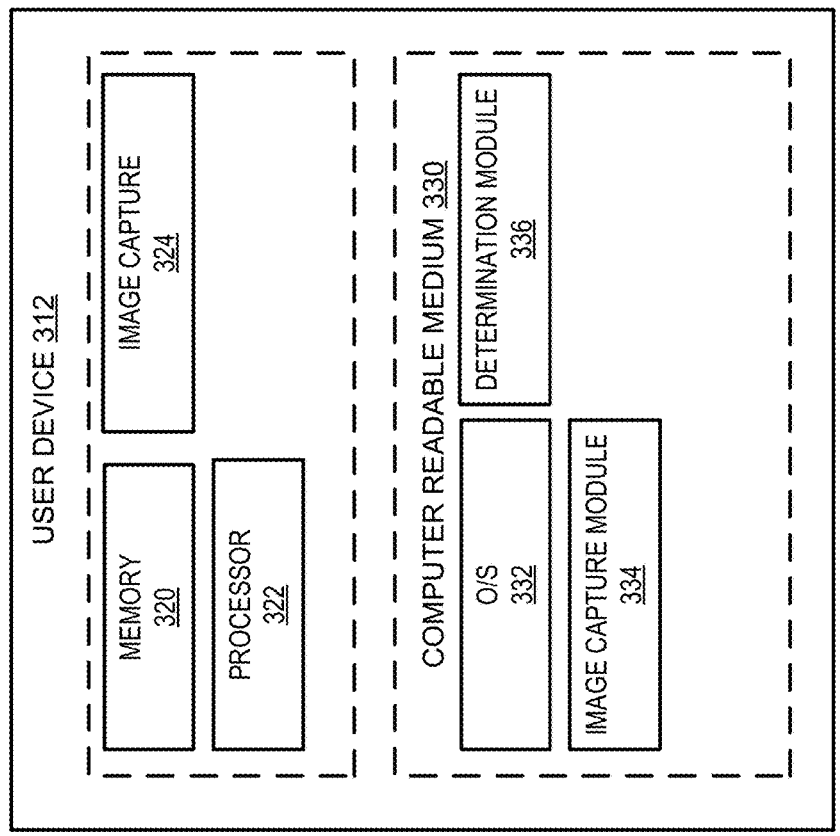
FIG. 3 illustrates a user device, in accordance with an embodiment of the disclosure.
Figure 4:
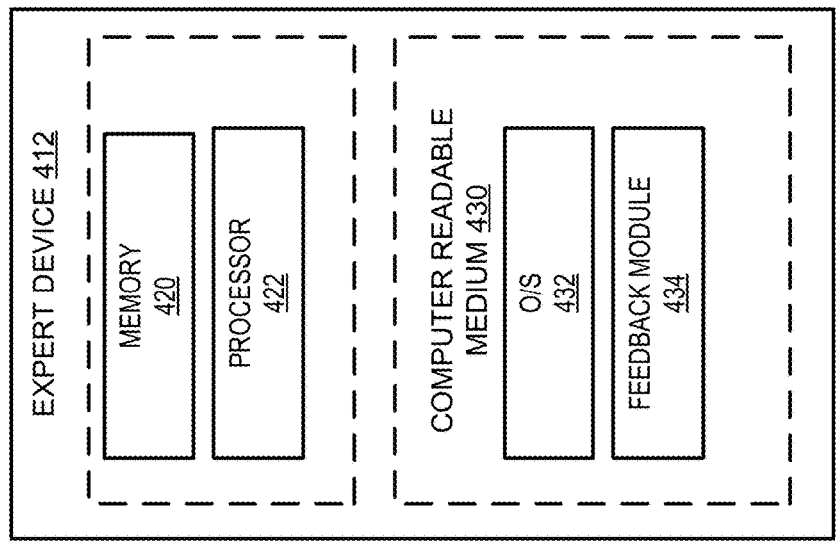
FIG. 4 illustrates an expert device, in accordance with an embodiment of the disclosure.

Medical condition system 102 may also be configured to communicate with a plurality of devices and data sources, including the data device 112 illustrated with FIG. 2, the user device 114 illustrated with FIG. 3, and the expert device 116 illustrated with FIG. 4.

FIG. 2 illustrates a data device, in accordance with embodiments of the disclosure. In illustration 200, data device 212 may include one or more memories 220, processors 222, and computer readable medium 230. Processor 222 may control a plurality of hardware or software connected to processor 222 by activating operating system 232 to perform processing of various functions described with modules of the system. For example, processor 222 may include instructions or data received from other elements and may process the loaded instructions or data, including data module 234. Various components of medical condition system 102 may be implemented with data device 212 as well. Data device 212 may incorporate the functionality of a mobile device (e.g., antenna, cellular module, etc.) for the electronic communication with network 110.

Data module 234 may be configured to provide images for use with the medical condition system 102. Data module 234 may transmit the images via network 110 to the medical condition system 102.

Data module 234 may supplement images provided by the user device 114 to help train and evaluate the models. Images provided by data module 234 may include images labeled by experts, including those labeled by dermatologists, dermatology textbooks, dermatology atlases, and validated data received from dermatologists in the integrated system network. Data from sources that are not reviewed may be provided to the review process to be labeled and expand the existing datasets.

FIG. 3 illustrates a user device, in accordance with embodiments of the disclosure. In illustration 300, user device 312 may include one or more memories 320, processors 322, and computer readable medium 330. Processor 322 may control a plurality of hardware or software connected to processor 322 by activating operating system 332 to perform processing of various functions described with modules of the system. For example, processor 322 may include instructions or data received from other elements and may process the loaded instructions or data, including image capture module 334. Various components of medical condition system 102 may be implemented with user device 312 as well. User device 312 may incorporate the functionality of a mobile device (e.g., antenna, cellular module, etc.) for the electronic communication with network 110.

User device 312 may be configured to capture one or more images or videos of medical conditions via image capture module 334. For example, image capture module 334 may be configured to allow a user to operate a camera or other image capture sensor 324 associated with user device 312 by directing the image capture sensor 324 at a medical condition to capture images or video of the medical condition for analysis. The medical condition images may be stored locally with memory 320, in a cloud data store associated with user device 312, or in a temporary storage. The image of the medical condition may be transmitted to medical condition system 102 via network 110.

Determination module 336 may be configured to receive medical condition predictions and corresponding probabilities from medical condition system 102 via network 110. Determination module 336 may receive an electronic file and provide the electronic file as an image to a display of patient user device 312.

FIG. 4 illustrates an expert device, in accordance with embodiments of the disclosure. In illustration 400, expert device 412 may include one or more memories 420, processors 422, and computer readable medium 430. Processor 422 may control a plurality of hardware or software connected to processor 422 by activating operating system 432 to perform processing of various functions described with modules of the system. For example, processor 422 may include instructions or data received from other elements and may process the loaded instructions or data, including feedback module 434. Various components of medical condition system 102 may be implemented with expert device 412 as well. Expert device 412 may incorporate functionality of a mobile device (e.g., antenna, cellular module, etc.) for the electronic communication with network 110.

Expert device 412 may be configured to receive image data and provide feedback via feedback module 434. For example, the image may be provided to a display on the expert device 412. In some implementations of the system, presenting images may include displaying images via an interface and providing a set of interface display elements.

The interface may provide a tool to provide feedback about the image (e.g., labeling the medical condition and associated label probabilities, information associated with the quality of the image, etc.). The information received via the interface may be transmitted via network 110 to medical condition system 102.

A plurality of expert devices 412 may provide feedback about a single image as detailed in the description of expert module 144, where the combined feedback may create a collection of expert opinions.

Method of Processing Medical Condition Data

Figure 5:
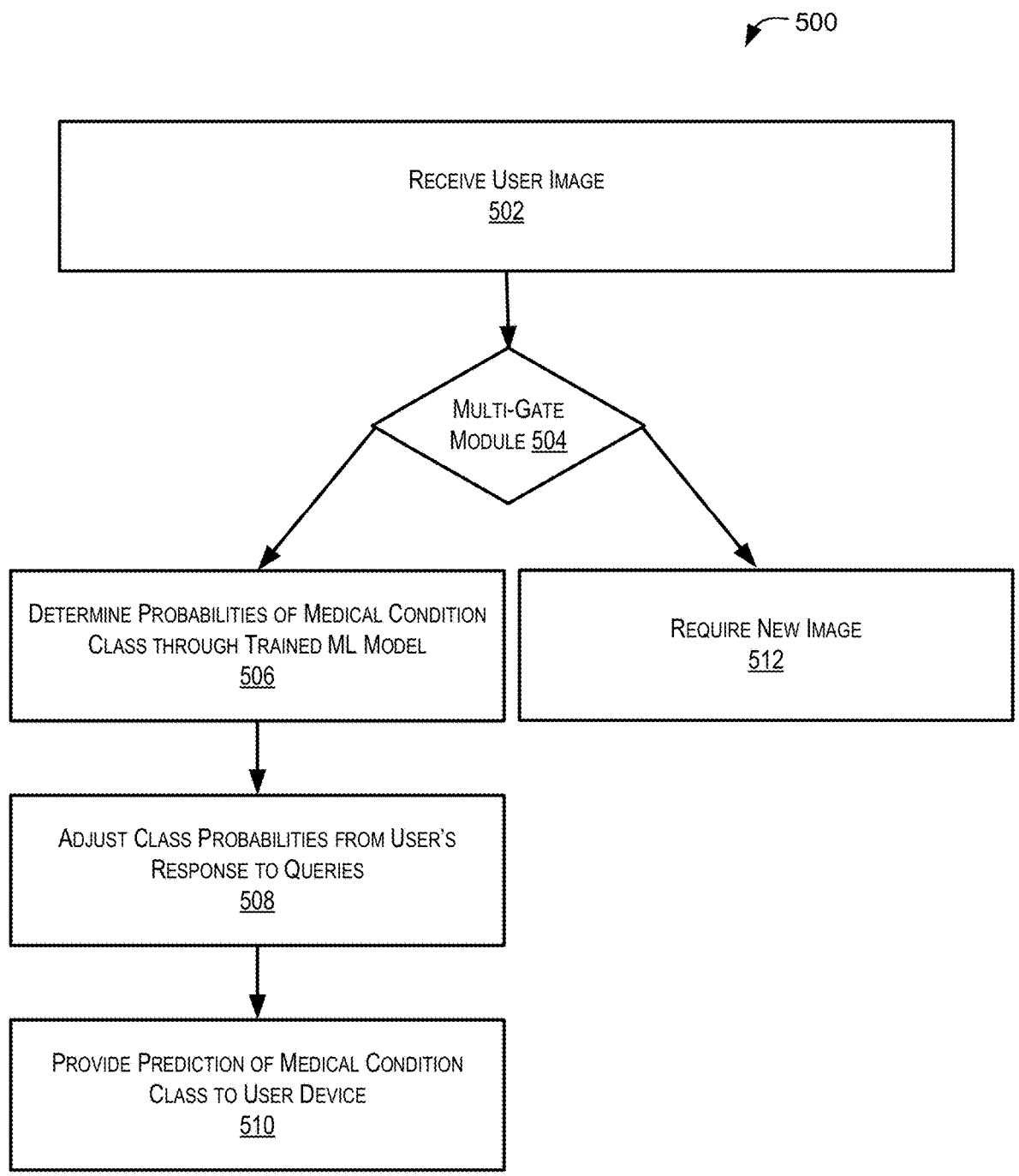
FIG. 5 illustrates a method to identify medical conditions given user input, in accordance with an embodiment of the disclosure.

FIG. 5 illustrates an example 500 of processing medical condition data, in accordance with an embodiment of the disclosure. At operation 502, via the user interface of user device 114, a user uploads one or more images (e.g., imaging a portion of the body that may have a medical condition) to the medical condition system 102 via network 110. The image is received by the medical condition system 102.

At operation 504, the images may pass through a multi-gate module, where the context within the images is detected using a visual classifier and user supplied information. Based on this detected context, the multi-gate module may apply context-specific actions. As an example, if the multi-gate module detects that an image does not meet the required parameters (e.g., does not contain skin or other body part) or if the image is of poor quality, the process may proceed to operation 512. At operation 512, the multi-gate module may determine the image to be "out of scope" and a new image may be required. The multi-gate module may also detect the type of image. For example, the multi-gate module may distinguish between dermoscopy images and non-dermoscopy images. Based on the detected image type, the image may be directed to a module designed for the specific type of image.

When the multi-gate module detects that an image meets the required parameters (e.g., contains skin or other body part) and/or is of good quality, the process may proceed to operation 506. Based on the detected context, at operation 506, artificial intelligence module 136 uses the image and determines predicted probabilities that the image falls into various medical condition classes. As users upload images, the system may make medical predictions and these images may be added to a review queue to be presented to a set of human experts for review. The system may evaluate how well the system's predictions match the experts' labels and corresponding probabilities. The prediction algorithms may be retrained with this information.

At operation 508, the visual classifier's predicted medical condition probabilities may be refined using question module 138, where questions may be presented to a user via user device 114 and the user's responses are incorporated to further refine the predicted medical condition probabilities. These questions may be based on the initial predicted medical condition probabilities made by artificial intelligence module 136 of medical condition system 102.

At operation 510, the predictions may be transmitted to user device 114. User device 114 may display a ranked list of potential medical conditions, their corresponding probabilities, additional information about the medical conditions and treatment options, and representative medical conditions images that may be similar to the user's uploaded image(s).

Method to Retrieve Similar Medical Condition Images

Figure 7:
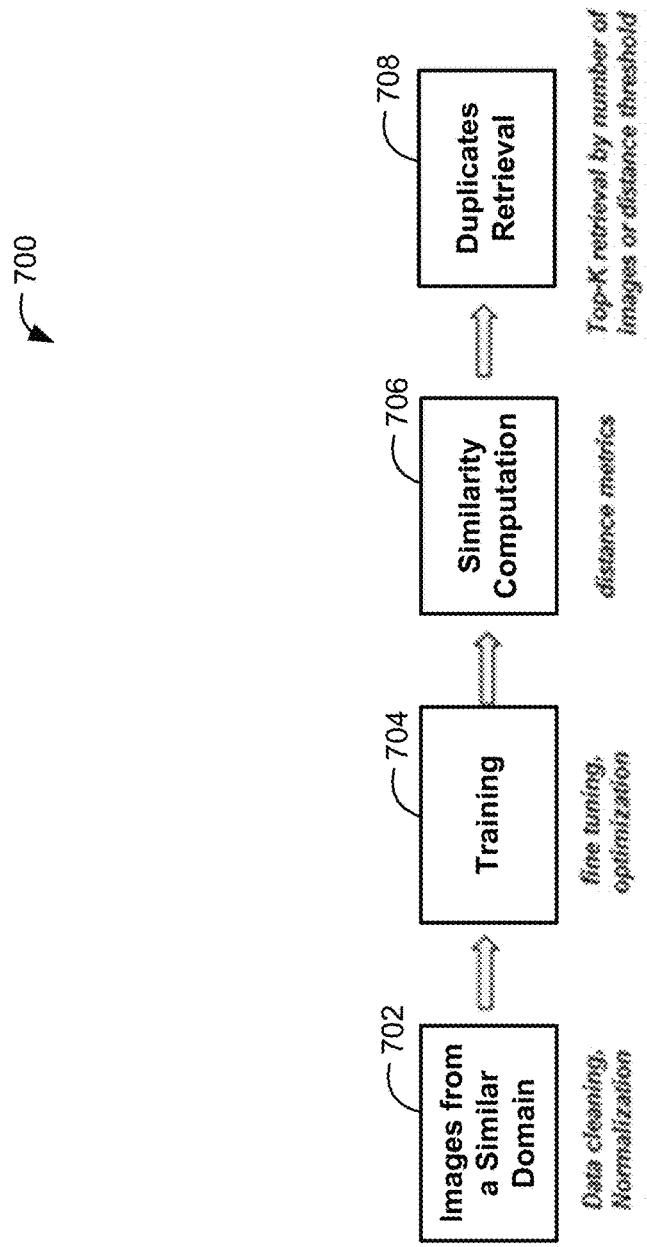
FIG. 7 illustrates an example of retrieving similar images, in accordance with an embodiment of the disclosure.

FIG. 7 illustrates one example of how the system may compress a representation of the image, in accordance with an embodiment of the disclosure. The image compression may summarize its two-dimensional spatial structure using, for example, one or more feature maps. Feature maps may be the learned image responses of specific convolutional CNN layers. Similar images may have similar feature maps.

In illustration 700, data are selected at operation 702. The medical condition system 102 may select data from a similar domain or modality (e.g., dermoscopic images) to train a machine learning model. This may help the model to identify discriminative features within a given domain.

At operation 704, medical condition system 102 may train one or more machine learning models to classify the medical diseases as described in artificial intelligence module 136, or be trained to recognize known visual properties associated with the disease.

At operation 706, one or more similarity metrics may be computed to compare and retrieve similar images. For example, the system may compute a measure of similarity between images using different similarity or distance metrics, such as cosine similarity, Euclidean distance, etc.

Operation 708 may implement a system to retrieve similar images based on the computed similarity or distance metric, where the images returned may be based on a sorted similarity ordering and the number of images to return may be based on a threshold, a fixed number of images, or a combination of both. The known medical condition labels from images similar to an uploaded image may be used separately or in conjunction with the visual classifier to infer predicted medical condition probabilities for the uploaded image. Images may be reviewed based on the ordered similarity to separate similar images across training 904, validation 906, and testing 908 data partitions.

Figure 8:
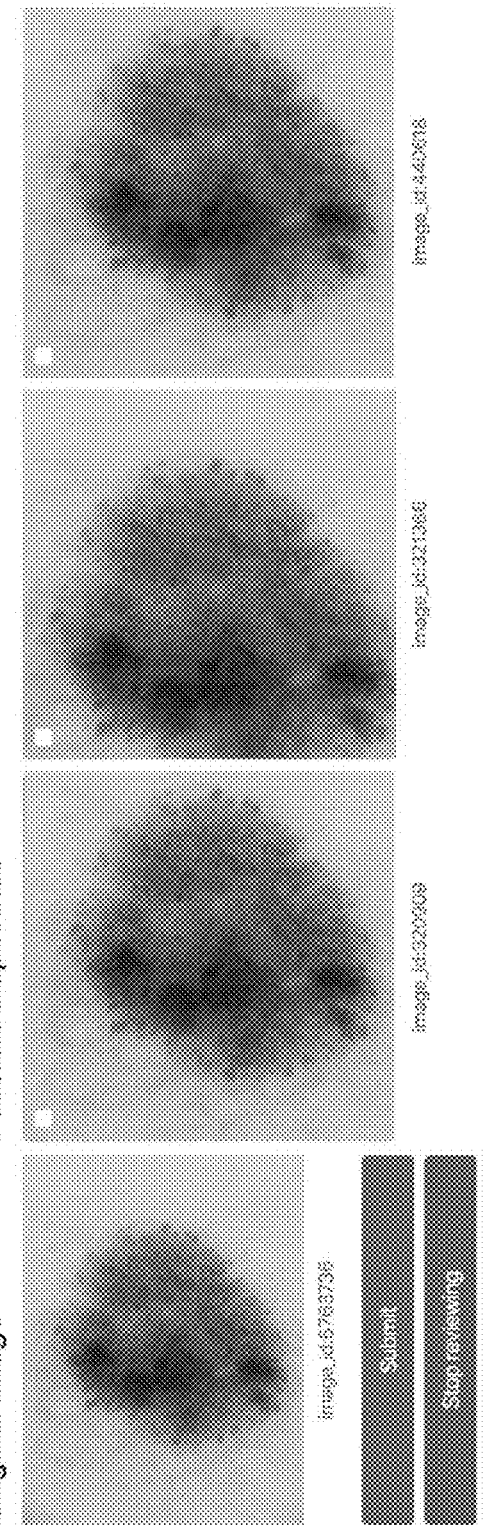
FIG. 8 illustrates one example of how the system may be used to determine similarity among images and/or perform image retrieval in order to retrieve similar images, in accordance with an embodiment of the disclosure.

FIG. 8 illustrates an example of image retrieval, in accordance with an embodiment of the disclosure. The illustrative example 800 shows an example where similar skin lesion images are retrieved by the system. Similar medical images may be retrieved even with changes in scale, translation, rotation, colour and illumination, and other non-affine transformations. Medical condition system 102 may be invariant to subtle changes in colour and illumination with affine and nonaffine transformations.

Methods of Generating a Training Data Pipeline

Figure 9:
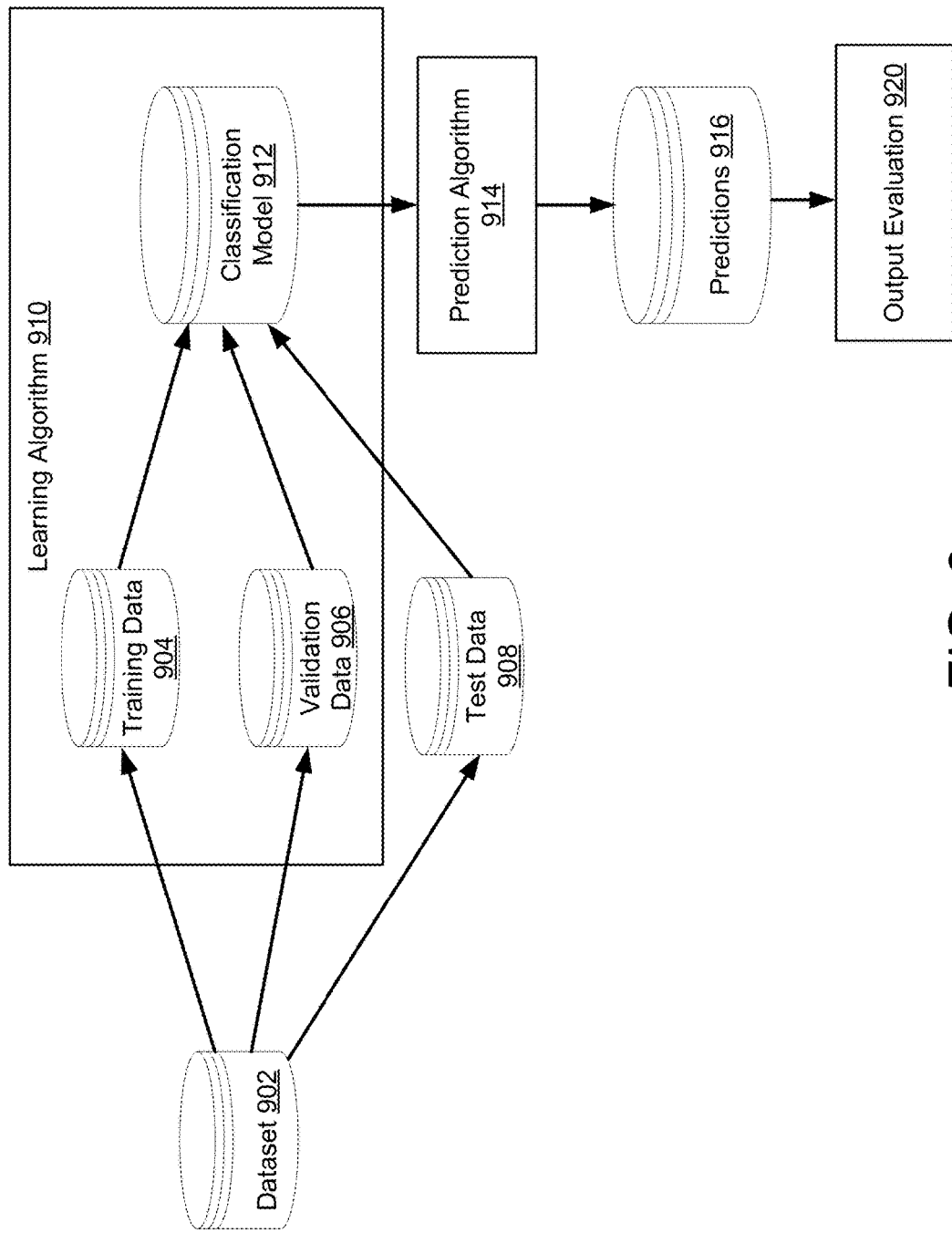
FIG. 9 illustrates one example of how the system may train and evaluate a machine learning model, in accordance with an embodiment of the disclosure.

FIG. 9 illustrates a pipeline to train the visual classification models used in the artificial intelligence module 136, in accordance with an embodiment of the disclosure. In illustration 900, data are received from various sources, including data device 112, user device 114, and expert device 116. Data may be stored in one or more datasets 902.

Data may be partitioned into training data 904, validation data 906, and test data 908. The data partitioning may incorporate the method to retrieve similar medical condition images in order to separate similar images across partitions. Learning algorithm 910 may rely on the training data 904 to train classification model 912 and validation data 906 to monitor the model performance during training. Test data 908 may be used to evaluate the performance of the trained classification model, as illustrated with examples 602, 604 in FIG. 6. Classification model 912 may be implemented as a convolutional neural network (CNN) or other type of deep learning model and various machine learning algorithms and optimization approaches may be implemented in embodiments of the disclosure, as described in artificial intelligence module 136.

The output from the classification model 912 is a list of predicted probabilities associated with each candidate medical condition, and may serve as input to the prediction algorithm 914. The prediction algorithm 914 uses these probabilities to decide on the set of predictions to assign to the image. For example, the prediction algorithm 914 may assign the top-k most probable medical conditions as the predicted labels for a given image. Output from prediction algorithm 914 may be stored with one or more predictions in predictions data store 916.

Test data 908 may be passed through the trained classification model 912 and the predictions algorithm 914 to determine the medical condition predictions 916. These predictions may be compared with known test data 908 labels to form an output evaluation 920 that indicates the system performance over test data 908.

Figure 10:
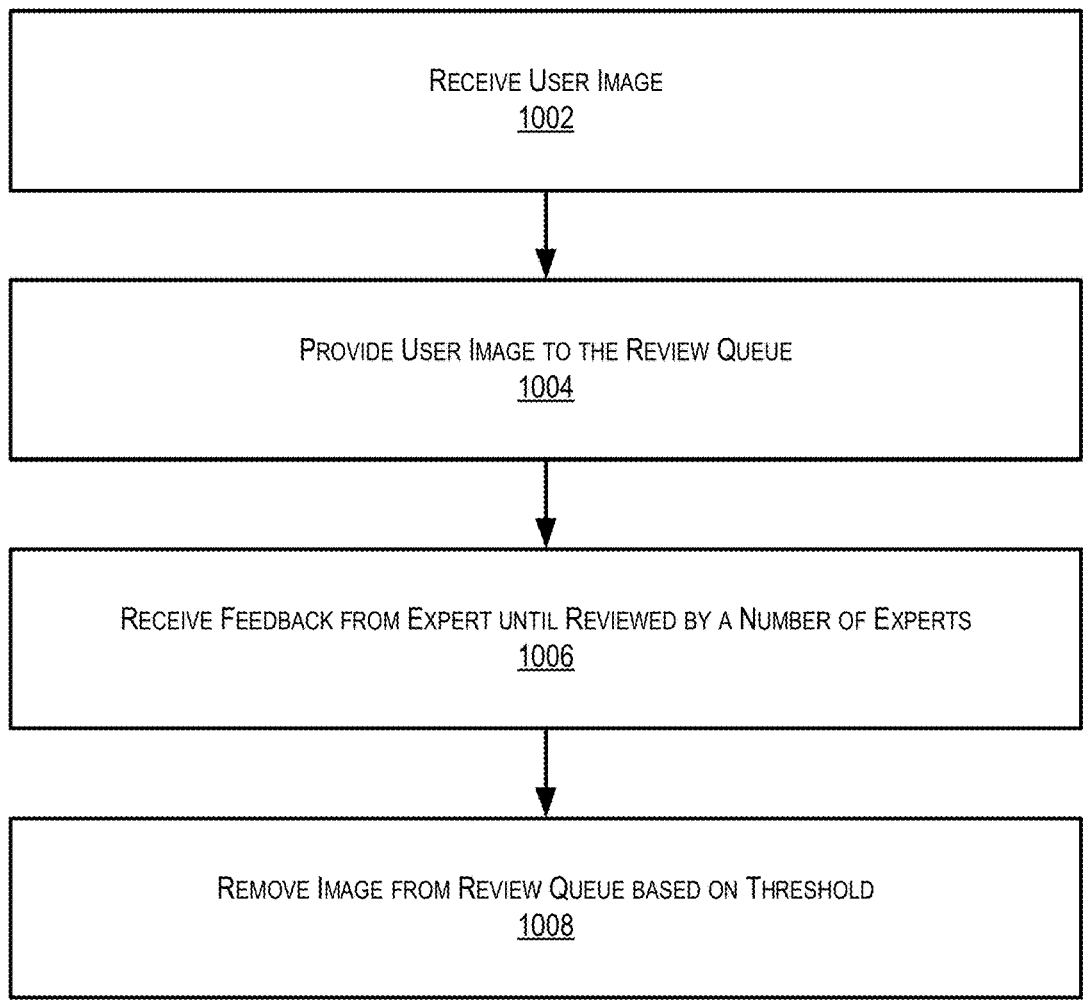
FIG. 10 illustrates a method to collect expert feedback, in accordance with an embodiment of the disclosure.

FIG. 10 illustrates a data processing pipeline to review data, in accordance with an embodiment of the disclosure. In illustration 1000, at operation 1002, a user may provide one or more images. At operation 1004, the image(s) may be sent to a review queue (as described in lab module 134) for review by one or more experts, including a global network of dermatologists.

Figure 11:
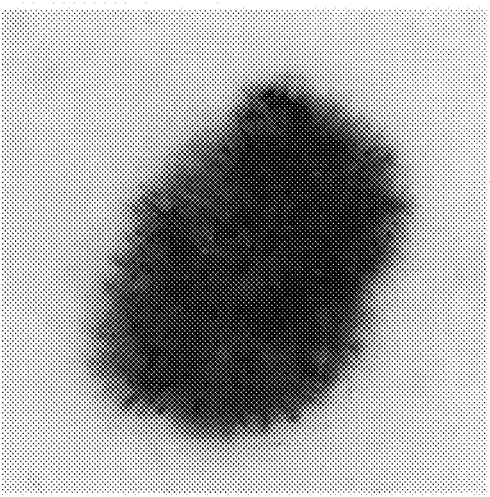
FIG. 11 illustrates an example interface for receiving feedback from experts, in accordance with an embodiment of the disclosure.

At operation 1006, the expert may be shown images and associated patient information and asked for feedback. The experts can access and systematically label images by assigning one or more labels and corresponding probabilities to an image. The system may track the labels and probabilities assigned by experts. An illustrative user interface for providing feedback is illustrated with FIG. 11.

The system may continue to receive feedback related to the image until a number of experts have provided feedback for the image. An image is considered validated and usable for training and evaluation once it receives feedback from M experts. These validated images may help identify conditions of concern and provides the system with additional data for evaluation and continued training. This allows the system to learn from perpetual use, ultimately improving the performance of the overall system.

At operation 1008, the image may be removed from the review queue upon meeting a second threshold value. For example, if Q experts indicate the image is of poor quality or the image is outside of the required parameters indicating the expected use case (e.g., image does not show a medical disease), the image may be removed from the review queue and deemed inadequate for dermatologists to identify without additional context.

ADDITIONAL CONSIDERATIONS

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the disclosure. For example, it is to be understood that the present technology contemplates that, to the extent possible, one or more features of any implementation can be combined with one or more features of any other implementation.

What is claimed is:

1. A system configured for determining medical conditions from images uploaded to a medical condition classification application that are processed within the medical condition classification application or uploaded to a server, the system comprising:
one or more hardware processors configured by machine-readable instructions to:
store one or more datasets of medical condition images, wherein the medical condition images are associated with one or more medical conditions as determined by human experts;
train a visual classifier model with the one or more datasets of the medical condition images;
receive, via a user interface of the medical condition classification application, one or more uploaded images;
pass the uploaded images through a visual classifier model to determine a context of the uploaded images;
generate an output of the visual classifier model representing predicted probabilities that the uploaded images exhibits one or more medical condition classes;
determine a set of predictions for the medical condition classes;
display the set of predictions that the uploaded images exhibit on a computer display via the user interface;
display information about the set of predictions;
display exemplar medical disease images of the set of predictions or medical disease that are similar to the uploaded images;
generate one or more datasets of validated images of medical conditions by:
generating a queue of images to be presented to the human experts, presenting a second image to a predetermined number of the human experts via the user interface, receiving and storing labels and corresponding probabilities for the second image from human experts, and combining reviews made by the human experts;
remove the second image from the queue; and
store the labels and corresponding probabilities with the second image.

2. The system of claim 1, wherein:
the machine-readable instructions for presenting the second image includes instructions for presenting the second image via one or more user interfaces, and providing a set of user interface display elements prompting the human experts to input whether the second image meets required parameters, appears to be of healthy skin or other body part, displays diseased skin or other body part and the probabilities of specified medical diseases, is a poor quality image, or a measure of the probability that a human expert of the human experts do not know how to correctly label the second image.

3. The system of claim 1, wherein the one or more datasets of validated images of medical conditions comprises labeled images mapped to an ontology which maintains relationships between dermatological conditions, the ontology comprising nodes representing medical conditions, which have parent-child relationships, and links relating medical conditions with broader labels to specific, situational disease labels.

4. The system of claim 3, wherein the one or more hardware processors are further configured by machine-readable instructions to organize the one or more datasets into a data structure comprising a hierarchical structure.

5. The system of claim 1, wherein the one or more hardware processors are further configured by machine-readable instructions to cause expert reviews of the uploaded images to be combined and provided to the user that uploaded the uploaded images in order for the user to receive the set of conditions that exist with the uploaded images based on an opinion of multiple experts.

6. The system of claim 1, wherein the uploaded images of a portion of a user's skin is received from a third party application, wherein the third party application comprises a telehealth or telemedicine application.

7. The system of claim 1, wherein the one or more hardware processors are further configured by machine-readable instructions such that the exemplar medical disease images of the set of predictions or medical disease that are similar to the uploaded images are identified based on a similarity metric.

8. The system of claim 1, wherein the one or more hardware processors are further configured by machine-readable instructions to:
pass the uploaded image through a multi-gate module and the multi-gate module is configured to distinguish between dermoscopy images and non-dermoscopy images; and based on a detected image type, direct the image to a module designed for the detected image type.

9. The system of claim 1, wherein the one or more hardware processors are further configured by machine-readable instructions to:
present a user interface through which an administrative user can create and manage image review tasks.

10. A system configured for determining medical conditions from images uploaded to a medical condition classification application that are processed within the medical condition classification application or uploaded to a server, the system comprising:
one or more hardware processors configured by machine-readable instructions to:
store one or more datasets of medical condition images, wherein the medical condition images are associated with one or more medical conditions as determined by human experts;
train a visual classifier model with the one or more datasets of the medical condition images;
receive, via a user interface of the medical condition classification application, one or more uploaded images;
pass the uploaded images through a visual classifier model to determine a context of the uploaded images;
generate an output of the visual classifier model representing predicted probabilities that the uploaded images exhibits one or more medical condition classes;
determine a set of predictions for the medical condition classes;
display the set of predictions that the uploaded images exhibit on a computer display via the user interface;
display information about the set of predictions;
display exemplar medical disease images of the set of predictions or medical disease that are similar to the uploaded images;
determine whether the uploaded image meets a stored set of required parameters considering images and additional user supplied information in a multi-gate module; and
pass the uploaded image through the multi-gate module, where the multi-gate module comprises a visual classifier, and (i) in response to determining that the uploaded image meets the stored set of required parameters, generate an output that directs the uploaded image to modality specific modules or (ii) indicates the uploaded image does not meet the stored set of required parameters.

11. The system of claim 10, wherein the one or more hardware processors are further configured by machine-readable instructions to:
pass the uploaded image through the multi-gate module and the multi-gate module is configured to distinguish between dermoscopy images and non-dermoscopy images; and based on a detected image type, direct the image to a module designed for the detected image type.

12. A system configured for determining medical conditions from images uploaded to a medical condition classification application that are processed within the medical condition classification application or uploaded to a server, the system comprising:
one or more hardware processors configured by machine-readable instructions to:
store one or more datasets of medical condition images, wherein the medical condition images are associated with one or more medical conditions as determined by human experts;
train a visual classifier model with the one or more datasets of the medical condition images;
receive, via a user interface of the medical condition classification application, one or more uploaded images;
pass the uploaded images through a visual classifier model to determine a context of the uploaded images;
generate an output of the visual classifier model representing predicted probabilities that the uploaded images exhibits one or more medical condition classes;
determine a set of predictions for the medical condition classes;
display the set of predictions that the uploaded images exhibit on a computer display via the user interface;
display information about the set of predictions;
display exemplar medical disease images of the set of predictions or medical disease that are similar to the uploaded images;
invoke a question module that selects and presents queries based on the predicted probabilities and confidence levels for the uploaded images;
receive responses to the queries via the user interface; and
iteratively present queries and refine the predicted probabilities based on the received responses.

13. The system of claim 12, wherein the one or more hardware processors are further configured by machine-readable instructions to:
pass the uploaded image through a multi-gate module and the multi-gate module is configured to distinguish between dermoscopy images and non-dermoscopy images; and based on a detected image type, direct the image to a module designed for the detected image type.

14. A method for determining medical conditions from images uploaded to a medical condition classification application that are processed within the medical condition classification application or uploaded to a server, the method comprising:
storing one or more datasets of medical condition images, wherein the medical condition images are associated with one or more medical conditions as determined by human experts;

training a visual classifier model with the one or more datasets of the medical condition images;
receiving, via a user interface of the medical condition classification application, one or more uploaded images;
passing the uploaded images through a visual classifier model to determine a context of the uploaded images;
generating an output of the visual classifier model representing predicted probabilities that the uploaded images exhibits one or more medical condition classes;
determining a set of predictions for the medical condition classes;
displaying the set of predictions that the uploaded images exhibit on a computer display via the user interface;
displaying information about the set of predictions;
displaying exemplar medical disease images of the set of predictions or medical disease that are similar to the uploaded images, wherein the one or more datasets of validated images of medical conditions is generated by;
generating a queue of images to be presented to the human experts, presenting a second image to a predetermined number of the human experts via the user interface, receiving and storing labels and corresponding probabilities for the second image from human experts, and combining reviews made by the human experts;
removing the second image from the queue; and
storing the labels and corresponding probabilities with the second image.

15. The method of claim 14, further comprising:
presenting the second image includes presenting the second image via one or more user interfaces, and presenting the second image includes providing a set of user interface display elements prompting a human expert of the human experts to input whether the second image meets required parameters, appears to be of healthy skin or other body part, displays diseased skin or other body part and the probabilities of specified medical diseases, is a poor quality image, or a measure of the probability that the human expert does not know how to correctly label the second image.

16. The method of claim 14, wherein the one or more datasets of validated images of medical conditions comprising of labeled images mapped to an ontology which maintains relationships between dermatological conditions, the ontology comprising nodes representing medical conditions, which have parent-child relationships, the method further comprising linking related medical conditions with broader labels to specific, situational disease labels.

17. The method of claim 16, further comprising:
organizing the one or more datasets into a data structure comprising a hierarchical structure.

18. The method of claim 14, further comprising:
presenting a user interface through which an administrative user can create and manage image review tasks.

19. The method of claim 14, wherein expert reviews of the uploaded image are combined and provided to the user that uploaded the uploaded image in order for the user to receive the set of conditions that exist with the uploaded image based on an opinion of multiple experts.

20. The method of claim 14, further comprising:
passing the uploaded image through a multi-gate module and the multi-gate module is configured to distinguish between dermoscopy images and non-dermoscopy images; and based on a detected image type, directing the image to a module designed for the detected image type.

21. A method for determining medical conditions from images uploaded to a medical condition classification application that are processed within the medical condition classification application or uploaded to a server, the method comprising:
storing one or more datasets of medical condition images, wherein the medical condition images are associated with one or more medical conditions as determined by human experts;
training a visual classifier model with the one or more datasets of the medical condition images;
receiving, via a user interface of the medical condition classification application, one or more uploaded images;
passing the uploaded images through a visual classifier model to determine a context of the uploaded images;
generating an output of the visual classifier model representing predicted probabilities that the uploaded images exhibits one or more medical condition classes;
determining a set of predictions for the medical condition classes;
displaying the set of predictions that the uploaded images exhibit on a computer display via the user interface;
displaying information about the set of predictions;
displaying exemplar medical disease images of the set of predictions or medical disease that are similar to the uploaded images, wherein:
determining whether a second image meets a stored set of required parameters by:
considering the second image and additional user supplied information in a multi-gate module, and passing the second image through the multi-gate module, where the multi-gate module comprises a visual classifier, and (i) in response to determining that the second image meets the stored set of required parameters, generating an output that directs the second image to modality specific modules or (ii) indicating the second image does not meet the stored set of required parameters.

22. The method of claim 21, further comprising:
passing the uploaded image through the multi-gate module and the multi-gate module is configured to distinguish between dermoscopy images and non-dermoscopy images; and based on a detected image type, directing the image to a module designed for the detected image type.

* * * * *